United States Patent
Peleg et al.

(10) Patent No.: US 11,266,180 B2
(45) Date of Patent: *Mar. 8, 2022

(54) HOT-WIRE CONTROL FOR AN ELECTRONIC CIGARETTE

(71) Applicant: Altria Client Services LLC, Richmond, VA (US)

(72) Inventors: Eyal Peleg, Tsoran (IL); David Cohen, Harei Yehuda (IL); Harold Brooks, Holliswood, NY (US); Dorron Levy, Givatayim (IL)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/458,869

(22) Filed: Jul. 1, 2019

(65) Prior Publication Data

US 2019/0320724 A1    Oct. 24, 2019

Related U.S. Application Data

(62) Division of application No. 15/599,639, filed on May 19, 2017, now Pat. No. 10,342,261, which is a
(Continued)

(51) Int. Cl.
*A24F 40/10* (2020.01)
*A24F 40/50* (2020.01)
(Continued)

(52) U.S. Cl.
CPC .............. *A24F 40/10* (2020.01); *A24F 40/50* (2020.01); *A24F 40/57* (2020.01); *A61M 15/06* (2013.01);
(Continued)

(58) Field of Classification Search
CPC .......... A24F 40/10; A24F 40/50; A24F 40/57; A61M 15/06
See application file for complete search history.

(56) References Cited

U.S. PATENT DOCUMENTS 4,746,961 A    5/1988 Konishi et al.
5,144,962 A    9/1992 Counts et al.
(Continued)

FOREIGN PATENT DOCUMENTS

| EP | 2110034 A1 | 10/2009 | |
| WO | WO-2009118085 A1 * | 10/2009 | .......... A24F 47/008 |
| WO | WO-2011146174 A2 | 11/2011 | |

OTHER PUBLICATIONS

International Search Report and Written Opinion dated Feb. 24, 2015 in International Application No. PCT/IB2014/001961.
(Continued)

*Primary Examiner* — Joseph S Del Sole
*Assistant Examiner* — Jerzi H Moreno Hernandez
(74) *Attorney, Agent, or Firm* — Harness, Dickey & Pierce, P.L.C.

(57) ABSTRACT

An electronic cigarette ("e-Cig") may include functionality for monitoring and controlling the thermal properties of the e-Cig. The system and method described herein may monitor a temperature based on a resistor (i.e. hot wire) near the wick and model the thermal cycle of an e-Cig. The model can be used for controlling the temperature of the e-Cig and preventing burning. The temperature control may dictate optimal conditions for atomization and smoke generation in an e-Cig while avoiding hotspots and burning to the atomizer or cartomizer.

12 Claims, 9 Drawing Sheets

Related U.S. Application Data division of application No. 13/939,987, filed on Jul. 11, 2013, now Pat. No. 9,814,262.

(60) Provisional application No. 61/670,143, filed on Jul. 11, 2012.

(51) Int. Cl.
| | |
|---|---|
| *A24F 40/57* | (2020.01) |
| *G01K 7/16* | (2006.01) |
| *G05D 23/19* | (2006.01) |
| *G05D 23/24* | (2006.01) |
| *A61M 15/06* | (2006.01) |

(52) U.S. Cl.
CPC ........... *G01K 7/16* (2013.01); *G05D 23/1919* (2013.01); *G05D 23/24* (2013.01)

(56) References Cited

U.S. PATENT DOCUMENTS

| | | | |
|---|---|---|---|
| 5,326,714 | A | 7/1994 | Liu et al. |
| 6,095,153 | A | 8/2000 | Kessler et al. |
| 9,814,262 | B2 * | 11/2017 | Peleg ................ G01K 7/16 |
| 10,226,078 | B2 * | 3/2019 | Peleg ................ A24F 40/46 |
| 10,342,261 | B2 * | 7/2019 | Peleg ................ A24F 40/00 |
| 2002/0142540 | A1 | 10/2002 | Katayama |
| 2002/0194500 | A1 | 12/2002 | Bajikar |
| 2006/0047368 | A1 * | 3/2006 | Maharajh ............ A61M 11/042 700/283 |
| 2008/0183801 | A1 | 7/2008 | Marton et al. |
| 2009/0095287 | A1 | 4/2009 | Emarlou |
| 2009/0095312 | A1 * | 4/2009 | Herbrich ............ A61M 11/042 131/273 |
| 2009/0133691 | A1 | 5/2009 | Yamada et al. |
| 2009/0320863 | A1 | 12/2009 | Fernando et al. |
| 2010/0024816 | A1 * | 2/2010 | Weinstein ............ A61M 11/042 128/203.27 |
| 2011/0036346 | A1 | 2/2011 | Cohen et al. |
| 2011/0209717 | A1 * | 9/2011 | Han .................... H05B 1/0291 131/273 |
| 2011/0265806 | A1 * | 11/2011 | Alarcon ................. A24F 47/00 131/273 |
| 2012/0047011 | A1 | 2/2012 | Rippetoe et al. |
| 2012/0048266 | A1 | 3/2012 | Alelov |
| 2012/0197090 | A1 | 8/2012 | Chen et al. |
| 2012/0199146 | A1 | 8/2012 | Marangos |
| 2012/0199572 | A1 | 8/2012 | Shen et al. |
| 2012/0227753 | A1 | 9/2012 | Newton |
| 2013/0042865 | A1 | 2/2013 | Monsees et al. |
| 2013/0074032 | A1 | 3/2013 | Barragan Barragan et al. |
| 2013/0081642 | A1 | 4/2013 | Safari |
| 2013/0104916 | A1 | 5/2013 | Bellinger et al. |
| 2013/0186392 | A1 | 7/2013 | Haartsen et al. |
| 2013/0200448 | A1 | 8/2013 | Yen et al. |
| 2013/0255702 | A1 | 10/2013 | Griffith, Jr. et al. |
| 2013/0298905 | A1 | 11/2013 | Levin et al. |
| 2013/0306084 | A1 * | 11/2013 | Flick ................... A24F 47/008 131/328 |
| 2013/0319435 | A1 * | 12/2013 | Flick ................... A61M 11/042 131/328 |
| 2013/0340775 | A1 | 12/2013 | Juster et al. |
| 2014/0014126 | A1 | 1/2014 | Peleg et al. |
| 2014/0020693 | A1 * | 1/2014 | Cochand ............ A61M 15/008 131/273 |
| 2014/0299137 | A1 | 10/2014 | Kieckbusch et al. |

OTHER PUBLICATIONS

International Search Report and Written Opinion dated Dec. 22, 2014 in International Application No. PCT/IB2014/001913.
Bo Li et al., "i-Function of Electronic Cigarette Building Social Network by Electronic Cigarette," 2011 IEEE International Conferences on Internet of Things, and Cyber, Physical and Social Computing, 2011, pp. 634-637.
U.S. Office Action dated Apr. 5, 2016 issued in U.S. Appl. No. 13/870,654.
U.S. Office Action dated Nov. 3, 2016 issued in U.S. Appl. No. 13/898,094.
International Preliminary Report on Patentability and Written Opinion dated Nov. 24, 2015.
U.S. Office Action dated Sep. 23, 2016 issued in U.S. Appl. No. 13/939,987.
U.S. Office Action dated Nov. 22, 2016 issued in U.S. Appl. No. 13/949,988.
U.S. Office Action dated Nov. 30, 2016 issued in U.S. Appl. No. 13/870,654.
European Office Action dated May 9, 2017 in European Application No. 14 786 269.2.
U.S. Office Action dated May 19, 2017 in U.S. Appl. No. 13/898,094.
U.S. Office Action dated Sep. 21, 2017 in U.S. Appl. No. 13/949,988.
Office Action dated Jun. 16, 2017 issued in U.S. Appl. No. 15/599,639.
Non-Final Office Action dated Jun. 14, 2018 in U.S. Appl. No. 15/933,552.
Non-Final Office Action dated Jul. 12, 2018 in U.S. Appl. No. 15/599,639.
Notice of Allowance dated Sep. 12, 2017 in U.S. Appl. No. 15/599,639.
Notice of Allowance dated Nov. 8, 2018 in U.S. Appl. No. 15/933,552.

\* cited by examiner

HOT-WIRE CONTROL FOR AN ELECTRONIC CIGARETTE

PRIORITY

This application is a Divisional of U.S. application Ser. No. 15/599,639, filed May 19, 2017, which is a Divisional of U.S. application Ser. No. 13/939,987, filed Jul. 11, 2013, which claims priority under 35 U.S.C. § 119(e) to U.S. Provisional App. No. 61/670,143, filed on Jul. 11, 2012, the entire contents of all of which are hereby incorporated by reference.

BACKGROUND

An electronic cigarette ("e-Cig") is a device that emulates tobacco cigarette smoking, by producing smoke replacement that may be similar in its physical sensation, general appearance, and sometimes flavor (i.e., with tobacco fragrance, menthol taste, added nicotine etc.). The device may use heat, ultrasonic energy, or other means to atomize/vaporize a liquid (for example based on propylene glycol, or glycerin, for example including taste and fragrance ingredients) solution into an aerosol mist. The atomization may be similar to nebulizer or humidifier vaporizing solutions for inhalation. The generated mist may be sensed similarly to cigarette smoke.

A common problem in electronic cigarettes ("e-Cigs") may be temperature management. The atomization of the liquid requires heating which may be difficult to regulate, Temperature control may be necessary for optimal timing of vaping (i.e. quick response time through the initial heating, for example in the first puff, when the e-Cig is still cool, or after a long break between puffs) without constant over heating that may be draining the battery too quickly unnecessarily. E-Cigs may require a high initial power output to begin the atomization process. The atomization process may be referred to as vaporization although vaporization may just be a secondary effect of the atomization, whereas atomization more accurately simulates smoke. The rapid increase in heat produced may not have enough time to dissipate, resulting in high temperatures internal and external to the housing of the cartridge. The c-liquid and the materials surrounding the heating element may start to overheat and may acquire an unpleasant burning smell (burn out) after reaching a high enough temperature, and the cartomizer housing may become so hot that it may be too warm to hold. Burning may occur when a cartridge filled with a liquid begins to become empty and the heating process occurs without proper control, which may result in bad taste and less pleasure when smoking.

Some e-Cigs use lithium-polymer cells that when fully charged start off with a high voltage of about 4.2 volts, and subsequently drop to about 3.0 volts as the cell's charge is depleted. The smoke/vapor/mist volume may be dependent on the power output. As the cell is depleted, the smoke volume may drop, which creates a less than optimal smoking experience. Accordingly, an e-Cig may not have a uniform and constant smoke volume and smoke temperature due to the variation in frequency and strength of puffs as well as the power output of the cell at any given time.

In particular, e-Cigs may have a circuit to reduce output power by regulating the voltage. The purpose of regulation may be to maximize the amount of puffs available from a fully charged battery as well as deliver a relatively constant voltage to the filament throughout the full smoking cycle. This may ensure that the user has a uniform experience from the first puff to the last, with no degradation in smoke/mist volume and smoke temperature as the battery discharges, while conserving energy and extending battery life. However, in order for a cartomizer to produce enough smoke/mist volume, it may need to be sufficiently warmed up, which may hard to achieve when the voltage is limited to this extent by the regulating circuit, A regulated voltage may therefore not supply enough power to satisfy the requirement for more priming needed to warm up the cartomizer, thus producing less smoke in the beginning, thereby impairing user experience. For a first-time user of the e-Cig, the first few weak puffs with little smoke volume may be a disappointing experience, possibly leading the first time user to discard electronic cigarettes altogether.

BRIEF DESCRIPTION OF THE DRAWINGS

The system and method may be better understood with reference to the following drawings and description. Non-limiting and non-exhaustive embodiments are described with reference to the following drawings. The components in the drawings are not necessarily to scale, emphasis instead being placed upon illustrating the principles of the invention. In the drawings, like referenced numerals designate corresponding parts throughout the different views.

DETAILED DESCRIPTION

Figure 1:
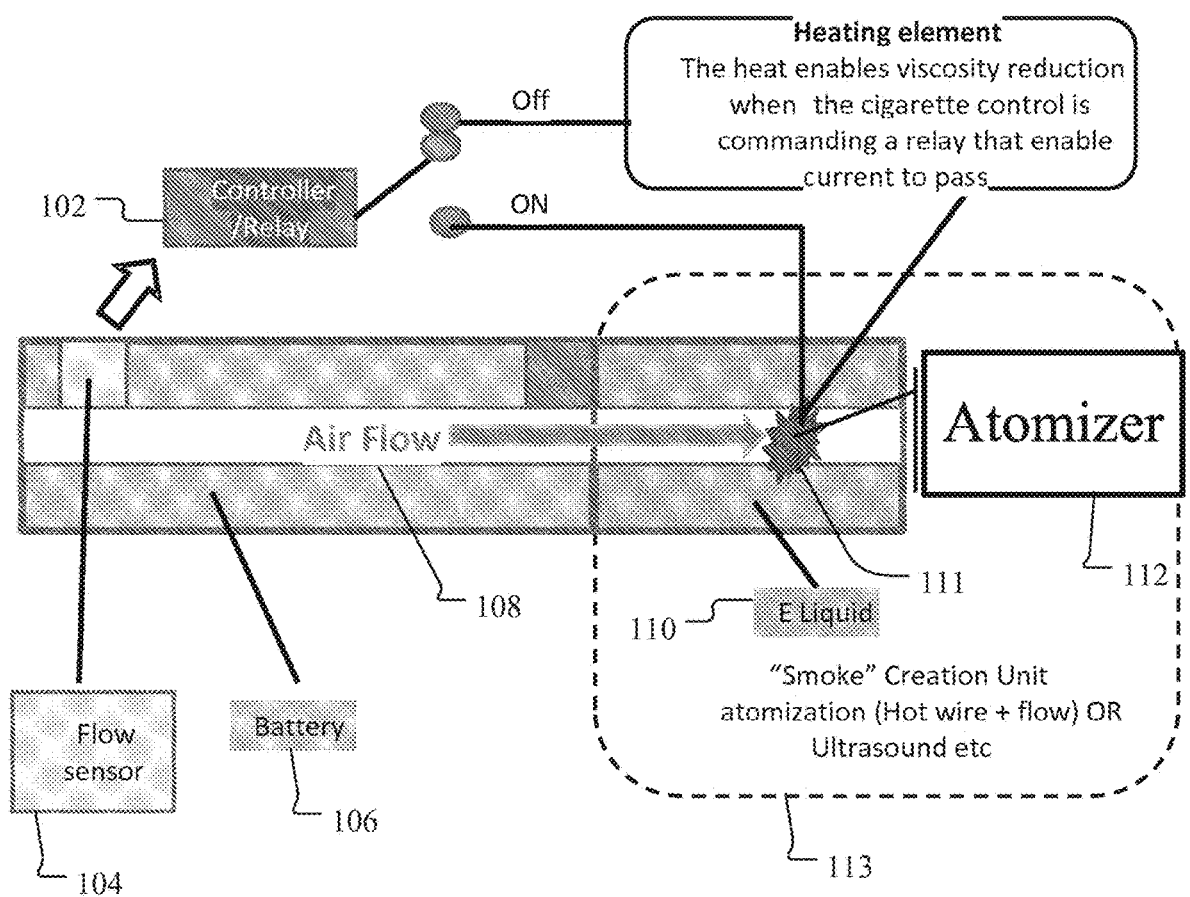
FIG. 1 is a diagram of an electronic cigarette.

By way of introduction, an improvement to an electronic cigarette ("e-Cig") may include a system and method that may model the thermal cycle of an e-Cig for controlling the temperature of the e-Cig and preventing burning. Temperature monitoring and control may improve the smoking (i.e. "vaping") experience of an e-Cig. Temperatures monitoring may be based on a resistor (i.e. hot wire) near the wick by which the resistance measurement is proportional to the temperature. The resistance may increase/decrease with temperature. In one embodiment, linear relationships may be assumed between resistance and temperature which is a close approximation to the relationship that exists in most metals.

The e-Cig may include a coil that wraps around the wick and the coil may act as a resistor and converts the electric energy into heat. A model of the thermal cycle of an e-Cig may be generated and used for controlling the temperature to create optimal conditions for atomization and smoke generation in an e-Cig while avoiding hotspots and burning to the atomizer or cartomizer. The monitoring, modeling and controlling may be part of a more dynamic power control program that provides a more optimal e-Cig that balances e-Cig product life, battery life, and user experience (e.g. quicker heating up for increased smoke/vapor volume in the first puff, and personalization of "smoke" properties for the user). Another possible temperature measurement technique may include a dedicated temperature-sensitive resistor ("thermistor") that is used to sense the temperature directly and is further described with respect to FIG. 2b. Another benefit may be derived from using the temperature to determine the amount of e-liquid left in the cartomizer. This may be done by monitoring the rate of climb that it takes to reach a given temperature.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, teams, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims. Nothing in this section should be taken as a limitation on those claims. Further aspects and advantages are discussed below.

FIG. 1 is a diagram of an electronic cigarette. The "smoke" produced by an e-Cig is a created by turning a liquid (e-Liquid 110) into mist and some vapor with an atomizer 112. The cartomizer 113 may include the atomizer 112 and the e-liquid 110. The cartomizer 113 may also be referred to as a cartridge throughout this disclosure and may be disposable. The c-liquid 110 may have a high viscosity at room temperature to enable longer shelf life and reduce leakages; however, this high viscosity may reduce the atomization rate or prevent atomization. The e-Liquid 110 is atomized via air flow 108, generated by the inhalation of the user (i.e. the smoker or consumer or vapor), which produces a pressure difference that removes e-Liquid droplets from the e-Liquid 110. In one embodiment, the e-Liquid 110 may be soaked in a wick. Although not shown in FIG. 1, the wick may be part of the cartomizer 113 and/or the e-Liquid 110. The wick is illustrated in and further described with respect to FIG. 2.

In order to reduce the e-Liquid viscosity, to a level enabling atomization, external heat may be applied through a heating element 111 as further described below. The heat (and over-heating) described herein may be from the heating element 111. Monitoring, modeling, and controlling of the heating element 111 may result in a more efficient e-Cig and a more pleasant vaping experience from the first puff until the cartomizer is depleted, with uniform, satisfactory smoke volume, avoiding burning unpleasant effects.

Ideally, the e-liquid 110 is preserved and long-lasting for a better user experience by avoiding evaporation and loss of volume, aromatic properties, etc. when the e-liquid is thick (with high viscosity). Conversely, e-liquid atomization requires liquid viscosity reduction while the user is puffing the cigarette, in order to enable satisfactory smoke volume generation and inhaling. Accordingly, a balance must be achieved for optimal performance. One way to reduce the e-liquid viscosity is by heating the c-liquid 110 with a heating element 111 that is turned on when a puff is applied by the smoker (for example triggered by a pressure difference sensor 104, which activates the battery when a puff is applied). Increased temperature may be an effective method to reduce the viscosity of most liquids, including the e-liquid.

In one embodiment, local viscosity reduction via heating, while inhalation occurs, enables c-Liquid atomization in the inhalation-generated flow of air 108. The e-Liquid 110 may be heated via an electric current flowing through the heating element 111 and may then be atomized (and/or partially evaporated) through the e-Cig and may contain taste and aroma—containing essence materials that collectively create a smoking sensation. The heating element 111 may also be referred to as a coil. In other embodiments, the heating element 111 may be a bar or another shape. The controller 102 may be activated due to air flow 108 (from the inhaled air) passing a flow sensor 104. As described below, the monitoring, modeling, and controlling of the temperature may be executed by the controller 102. In particular, the controller 102 may receive inputs (e.g. resistance measurements), model a thermal cycle of the e-Cig, and based on the modeled thermal cycle of the e-Cig, may control the temperature and modify the behavior of the e-Cig for optimal usage.

The sensor 104 may be activated by the pressure drop across the sensor and may directly switch the battery 106 power on, or be used as an input for the controller 102 that then switches the battery 106 current on. Although illustrated as separate from the e-Cig, the controller 102 may be a part of the e-Cig (e.g. along with the battery 106). The battery 106 may be a separate/removable assembly. The battery 106 may include one or more electronic chips controlling and communicating from it. It may connect with the cartomizer 113, which can be replaced or changed (e.g. when a new/different c-Liquid 110 is desired).

For the smoke volume, temperature, smell, taste and feel to be optimal from the first puff, enough heat must be applied to the coil to heat up enough liquid volume, utilizing for example the lower viscosity to atomize the c-liquid, which in turn will turn into atomized smoke and some vapor. The heat applied to the coil is drawn away by for example the atomization process, by evaporation, by heating the cartomizer walls, the reservoir of e-liquid (including the c-liquid within the wick), and/or by the adjacent air—all as a function of time, puff rate, room temperature and other factors. The temperature may not be stable by its own nature and may vary as the e-Cig is smoked, during the puff, between puffs, and throughout the e-Cig and the cartomizer Consequently, the smoking experience may vary, even during one smoking session, and negative effects such as burning may appear without modeling and controlling as described below.

The e-Cig may include two parts. The first part is often just referred to as the battery or battery portion (i.e. battery enclosure) and it includes the battery, the air flow sensor and the controller. The second part is the cartridge (i.e. cartomizer 113) that is filled up with liquid and flavors that is required for smoke and flavor generation. The battery portion and the cartridge may be connected by metal connectors. An airflow tube of the battery enclosure and an airflow tube of the cartridge may enable the smoker to puff through the e-Cig and activate the airflow sensor inside the battery portion. This may trigger the controller and create an electrical flow through the coil inside the cartridge which is heated due to the conversion of electrical energy to heat. This reduces viscosity and helps atomize the liquid that is in the cartridge at the vicinity of the coil and causes smoke (i.e. atomized micro-droplets). The process is further explained below in FIG. 2.

Figure 2A:
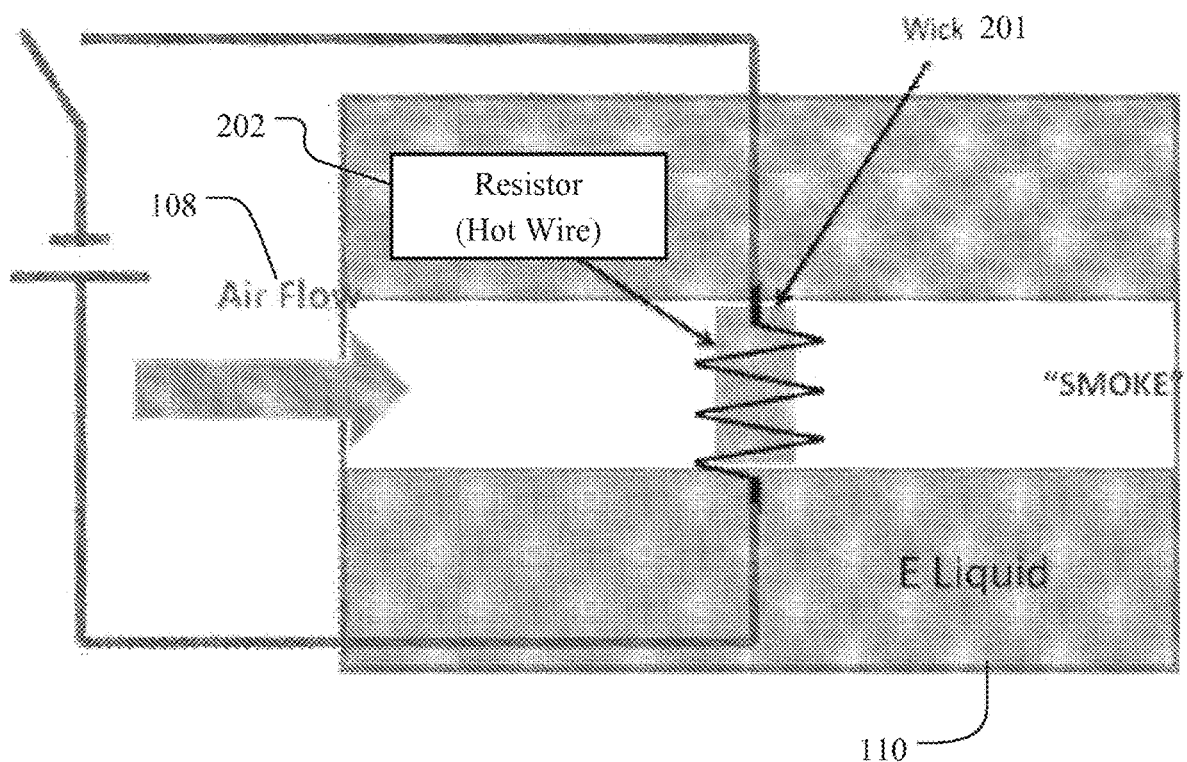
FIG. 2a is a diagram of a portion of a cartomizer with a wick.

FIG. 2 is diagram of a portion of a cartomizer with a wick. The e-liquid 110 of the cartomizer is shown receiving the air flow 108 as in FIG. 1. The air flow 108 may pass a wick 201 that is located adjacent a resistor 202. The resistor 202 may also be referred to as a hot wire.

The heating is typically not applied to the bulk of the e-liquid (for example to avoid unnecessary evaporation of taste and smell agents, or the viscosity reduction of the e-liquid, leading possibly to leaks), but to a portion of it, that exists in the wick 201. The wick 201 may be wrapped around a heating element. As the puff is applied, a sensor triggers the battery to let current flow through the heating element, heating the liquid in the wick and promoting viscosity drop. The now heated (i.e. thin or low viscosity) liquid can be atomized by the air flow 108, creating the mist that is felt by the smokers as smoke Temperature instability may be created if the air flow 108 is non-uniform across the cartomizer inner cross-section. Since, the wick 201 may be hottest near the coil non-uniform air flow may cause temperature variations. Another source for temperature variation may be the unevenness of flow velocity over the length of the cartomizer. Due to viscosity shear forces are created and the flow may be stopped near the edges (e.g. for theoretical flow in a pipe, which describes the air flow 108). Based on these temperature variations, modeling of the thermal variances may be used for optimizing the e-Cig performance. The methods and processes described below for monitoring, modeling, and compensating for thermal variances may be performed by or with the controller 102.

Figure 2B:
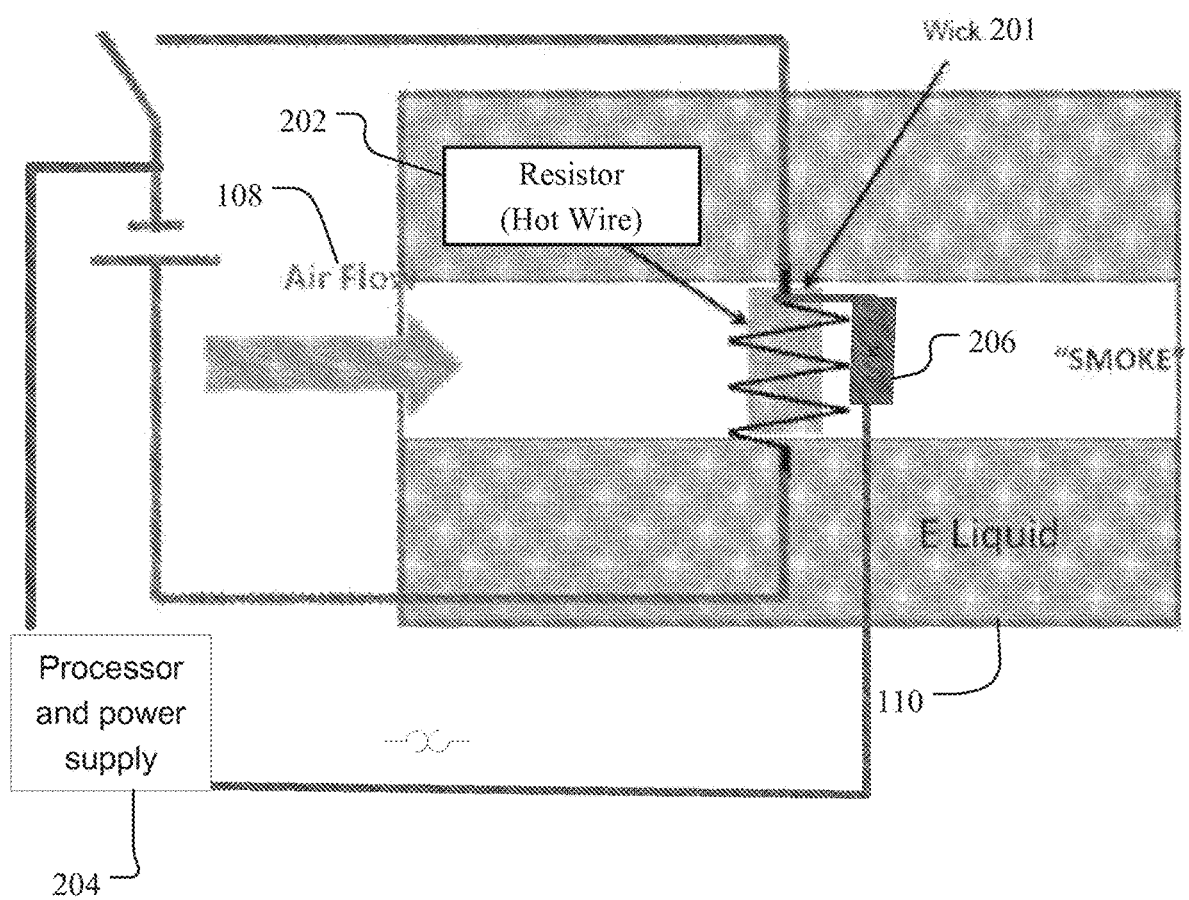
FIG. 2b is a diagram of a portion of a cartomizer with a wick and heat measurement element.

FIG. 2b is a diagram of a portion of a cartomizer with a wick and a heat measurement element 206. In particular, FIG. 2b illustrates a separate heat measurement element 206 such as thermopile or thermistor that may be placed close to the coil and enable temperature measurement rather than using the coil or resistor 202. FIG. 2b further illustrates that a processor and power supply 204 (which may be separate elements but are shown as one for simplicity) communicates with the cartomizer. The processor 204 may control the heat measurement element 206 and receive the temperature measurements.

Figure 3:
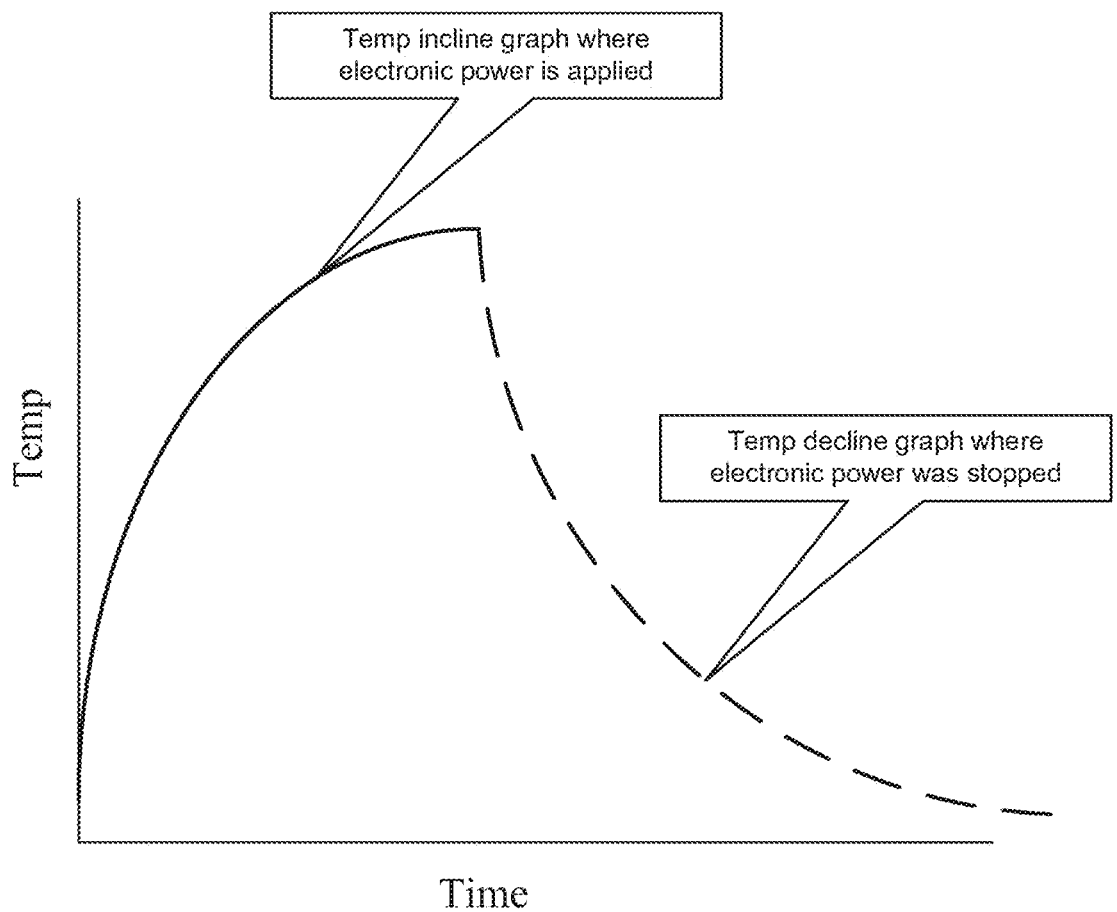
FIG. 3 is a chart illustrating an exemplary thermal cycle for an e-Cig.

FIG. 3 is a chart illustrating an exemplary thermal cycle for an e-Cig. The temperature increases where electronic power is applied. Likewise, the temperature decreases when electronic power is stopped. Accordingly, the modeling of the thermal cycle may be used to control the electronic power input, which may be used for optimizing the temperature variance of the e-Cig.

The heating may be triggered by the puff (e.g. incoming air flow 108) that also cools the coil and its environment. However, cooling is at non-uniform rate, as the flow speed and volume changes during the puff. A portion of the heating/cooling cycle (i.e. thermal variation cycle or thermal cycle) happens after the puff has ended, adding variability to the conditions. The e-liquid by conduction, convection, atomization and evaporation may remove heat from the system in addition to heat transferred by the coil and the wick; then remaining e-liquid may also be able to retain heat, which changes the initial conditions for each puff, for example, in a consecutive closely-spaced puffs series.

During the heating phase, inhaled air may create forced convection and heat transfer front the wick (in one embodiment) is subjected to changes in convection due to change in air velocity as well as additional factors including atomization, evaporation and inflow of colder e-liquid to the wick. Diminishing liquid quantity and a soon-to-be-exhausted cartomizer may change the transient conditions further, possibly allowing for higher temperature, even above the safe level. A safe level may include a mixture of vapor/mist and hot air at or around ideal conditions, or to avoid burning. This behavior may be utilized to identify an exhausted cartomizer early. In order to overcome the innate transient nature of the e-cig thermal cycle while in use, the e-Cig may be modeled as a dynamic system with basically periodic behavior. The theory may assume that the temperature curve behaves as if the coil thermal mass is small relative to the environment. This allows the application of simplified models, and which may be confirmed by empirical results.

The modeling of the thermal cycle may utilize equations that assume the control volume that involve the coil the wick and the liquid within it have certain simplified properties. These assumptions match with experimental data. The assumptions include: 1) minimal mass transfer to environment; 2) the temperature of environment is almost constant; 3) thermal coefficients do not modify with temperature; and/or 4) the control volume (the internal of the cartomizer around the coil and wick) behaves as a single point assuming that internal heat transfer is much faster than heat transfer to environment therefore the temperature in the control volume may be the same at any point. Accordingly, the basic heat transfer equation is:

$$\frac{T(t) - T{final}}{T{start} - T{final}} = \text{Exp}^{\frac{-t}{Tau}} \quad \text{Equation (1)}$$

Where T(t) is temperature at time t, Tf is the final temperature, Ts is the start temperature. Tstart may be any point in the decline curve and Tfinal may be the point where the steady state is reached. Tau is a heat transfer time constant that may be calculated by:
1) Selecting Tfinal;
2) Applying logarithmic annotation on both sides of equation (1) such that $$\ln\left(\frac{T(t) - Tfinal}{Tstart - Tfinal}\right) = \frac{-t}{Tau} \quad \text{Equation (2)}$$

3)

$$Tau = \frac{-t}{\ln\left(\frac{T(t) - Tfinal}{Tstart - Tfinal}\right)} \quad \text{Equation (3)}$$

However, Tfinal may not be always reached and curve shape may be slightly different. Tfinal may be limited to lower values of any selected point. Accordingly, a vector with various values of optional Tfinal may be created such that TfinalV=[Tfinal(1), Tfinal(2), . . . ,] and all these values may create alternative curves and the curve that have minimal error to original result may be selected. Each component of T0V may be treated as a source to calculate a more accurate Tau.

$$Tau(j) = \frac{-t}{\ln\left(\frac{T(t) - Tfinal(j)}{Tstart - Tfinal(j)}\right)}, J = 1, 2, \ldots \quad \text{Equation (4)}$$

Where TfinalV=[Tfinal(1), Tfinal(2), . . . ,]. Synthetic curves may be created with a form identical to equation 1:

$$Tsynthetic(t) = (Tstart - Tfinal(j)) * \text{Exp}^{\frac{-t}{Tau(j)}} + Tfinal(j) \quad \text{Equation (5)}$$

The curve of Equation (5) that may be closer to original measured results can be selected. The selected synthetic curve may fit to a certain Tfinal and Tau.

If the initial tau is smaller and final is higher, then both values decrease. The physical explanation may be due to environment cooling with a reduction of liquid ability to carry heat as viscosity increases when the temperature drops. In other words, the explanation may be that as temperature decreases, the environment is heated. Through empirical analysis, it may be confirmed that the temperature variations inside the cartomizer during a sequence of puffs may be effectively approximated by the series of equations discussed above. Fitting an exponential function to the measured temperature change over time provides a good fit; however, even better accuracy may be achieved while dividing the curve into two parts, upper and lower. The fit can be divided in various ways, not only into two parts, as fits this one embodiment. The differences between the upper and lower parts might be attributed to changing viscosity of the c-liquid during cooling, leading to changes in the ability of the e-liquid to transfer heat by convection. Although the division to upper and lower parts fits to empirical results, other divisions are possible.

Exemplary experimental data is shown in the following Table 1:

| | | Calculated parameters | | | | |
|---|---|---|---|---|---|---|
| | Time from | Whole downslope | | Upper part | | Lower part | |
| Point | start | Tau | Tfinal | Tau | Tfinal | Tau | Tfinal |
| 1 | 9 | 1 | 84 | 0.4 | 105 | 1.5 | 77 |
| 2 | 67 | 0.9 | 106 | 0.5 | 122 | 1.5 | 99 |
| 3 | 139 | 0.9 | 110 | 0.4 | 126 | 1.6 | 101 |
| 4 | 207 | 1.1 | 112 | 0.7 | 128 | 1.4 | 107 |
| 5 | 236 | 1.1 | 113 | 0.8 | 129 | 1.4 | 109 |
| 6 | 272 | 1.6 | 111 | 1.1 | 130 | 1.8 | 108 |
| 7 | 296 | 2.1 | 108 | 1.2 | 138 | 3 | 90 |
| 8 | 320 | 4 | 85 | 2.4 | 132 | 4.5 | 74 |
| 9 | 350 | 3.8 | 100 | 3.3 | 115 | 4.7 | 78 |
| 10 | 533 | 2.9 | 64 | 2.6 | 69 | 3.4 | 60 |

Table 1 illustrates that after about 300 seconds the Tau is increasing rapidly. Generally, Tau is stable throughout the lifetime of the e-Cig, but increases rapidly with e-liquid depletion (i.e. the approach possibly to a burning condition). The shape and time constant calculation may not be dependent on final temperature as can be found when point No 10 in Table 1 is analyzed: the temperature that is reached is low however the e-Cig heat transfer time constant remain high.

Figure 4:
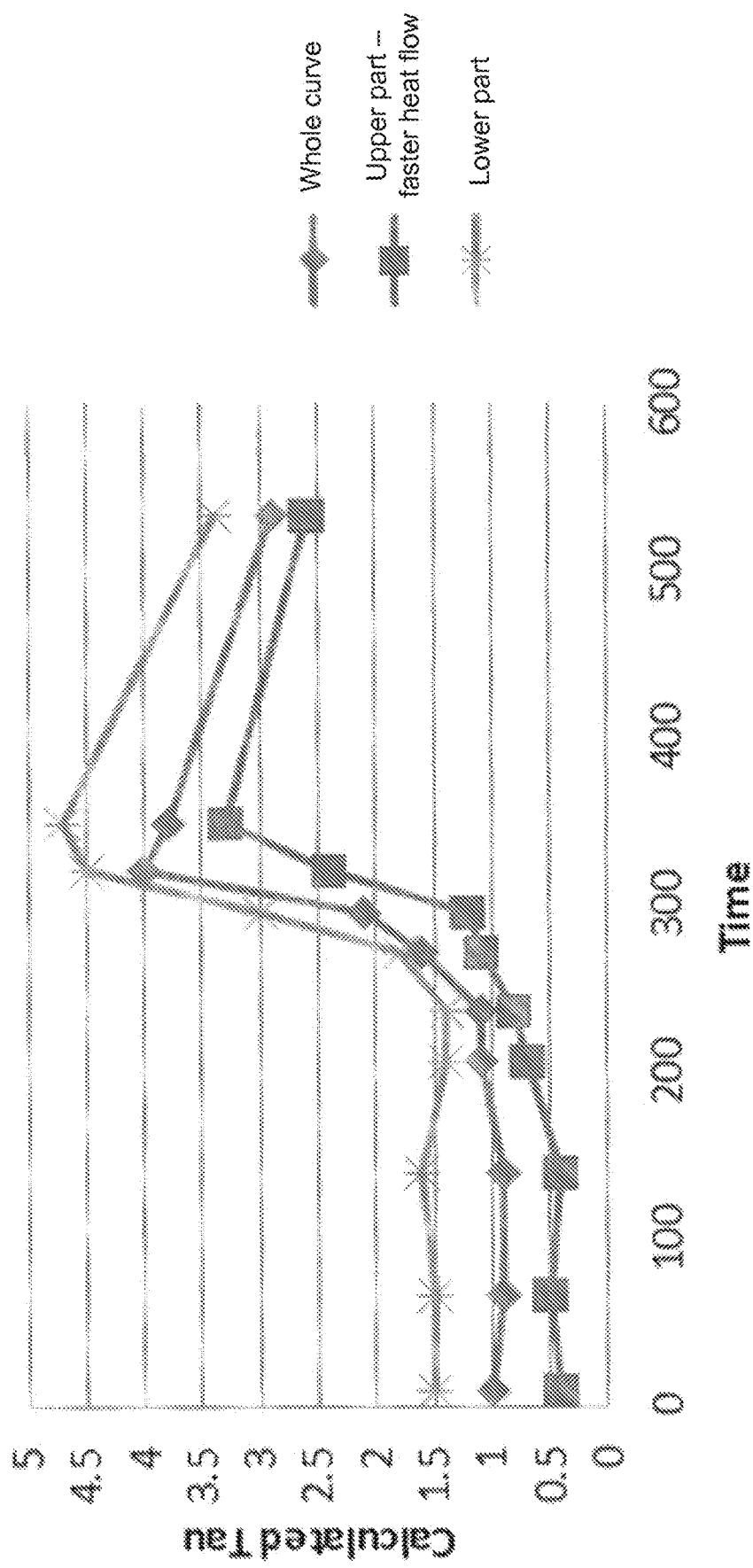
FIG. 4 is a chart that illustrates the heat transfer time constant behavior over time.
Figure 5:
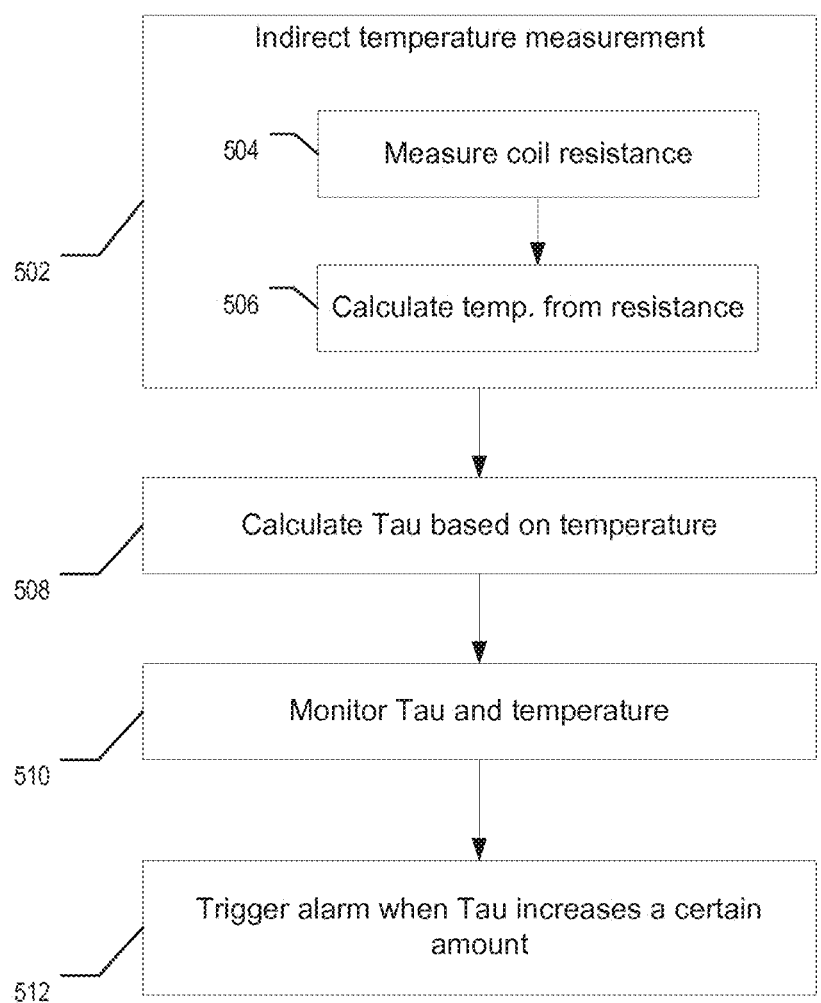
FIG. 5 illustrates the modeling and control of an e-Cig based on thermal variance.

FIG. 4 is a chart that illustrates the heat transfer time constant behavior over time. The behavior of Tau can be used as an alert when the e-liquid is about to be depleted. This may prevent the misuse of the e-Cig, for example if storage conditions have depleted the liquid before it was ever used. In particular, when Tau has an increase, it may be an indication that the e-liquid is becoming depleted and this warning may prevent a burning scenario, for example by alerting the user (by means of some indication, for example blinking LED at the e-Cig tip, message communicated via some communication mean, or even just shut down of the e-Cig). Identifying the point when to discard the cartomizer may be accomplished using a follow-up algorithm, such as Statistical Process control (SPC), to point out the first indication of Tau change (e.g, a bit above 300 in Table 1 and FIG. 4), This calculation may be used to warn the user to stop using the e-Cig because a burning situation may occur shortly. In one example, when Tau increases to a certain level above the previous average (e.g. the warning point may be two standard deviations), the e-Cig may stop the use of the cartomizer entirely. This modeling may apply to various users and smoking habits because Tau may be different from smoker to smoker (and may still be inside an acceptable range, lower than the Tau of a depleted-e-liquid e-Cig); the application of tools like SPC allows for locating the point of change of Tau even if Tau's average value differs between e-Cigs, users, environmental conditions, etc. This method of calculation may be done for Tau of any part of the curve and to the calculated T0 of any part, of the curve, FIG. 5 illustrates the modeling and control of an e-Cig based on thermal variance. The modeling with Tau may be used for identifying when the e-liquid is running out and when a burning situation is likely to occur. As illustrated in FIG. 5, the calculation of Tau may rely on an indirect temperature measurement in block 502. In one embodiment, the processor of the battery may not enable use of the e-Cig until the cartomizer is replaced.

A coil resistance is calculated in block 504. The temperature measurement may be calculated based on the coil resistance in block 506. Since the electrical resistance of a conductor such as a copper wire might be dependent upon collisional processes within the wire, the resistance may be expected to increase with temperature since there will be more collisions. An intuitive approach to temperature dependence leads one to expect a fractional change in resistance which is proportional to the temperature change:

$$\frac{\Delta R}{R_0} = \alpha \Delta T \quad \alpha = \text{temperature coefficient of resistance.}$$

Or, expressed in terms of the resistance at some standard temperature from a reference table;

$$\frac{R - R_0}{R_0} = \alpha(T - T_0) \text{ or } R = R_0[1 + \alpha(T - T_0)]$$

As one example if a resistor of initial value $R_0=100$ ohms at initial temperature $T_0=130$ C is heated 10 temperature $T=150$ C and has a temperature coefficient $\alpha=5\times10^{-3}/C$ then the resistance will be R=110.0000 ohms. The resistivity and temperature Coefficient at 20 C are shown in the following table:

| Material | Resistivity (ohm m) | | Temperature coefficient per degree C. | Conductivity $\_ \times 10^7/10$ m |
|---|---|---|---|---|
| Silver | 1.59 | $\times10^{-8}$ | .0061 | 6.29 |
| Copper | 1.68 | $\times10^{-8}$ | .0068 | 5.95 |
| Aluminum | 2.65 | $\times10^{-8}$ | .00429 | 3.77 |
| Tungsten | 5.6 | $\times10^{-8}$ | .0045 | 1.79 |
| Iron | 9.71 | $\times10^{-8}$ | .00651 | 1.03 |
| Platinum | 10.6 | $\times10^{-8}$ | .003927 | 0.943 |
| Manganese | 48.2 | $\times10^{-8}$ | .000002 | 0.207 |
| Lead | 22 | $\times10^{-8}$ | . . . | 0.45 |
| Mercury | 98 | $\times10^{-8}$ | .0009 | 0.10 |
| Nichrome (Ni, Fe, Cr alloy) | 100 | $\times10^{-8}$ | .0004 | 0.10 |
| Constan-tan | 49 | $\times10^{-8}$ | . . . | 0.20 |
| Carbon* (graphite) | 3-60 | $\times10^{-5}$ | -.0005 | . . . |
| Germanium* | 1-500 | $\times10^{-3}$ | -.05 | . . . |
| Silicon* | 0.1-60 | . . . | -.07 | . . . |
| Glass | 1-10000 | $\times10^{-9}$ | . . . | . . . |
| Quartz (fused) | 7.5 | $\times10^{-17}$ | . . . | . . . |
| Hard rubber | 1-100 | $\times10^{-13}$ | . . . | . . . |

Temperature sensing through the coil's resistance, and quick current flow modulation, may result in uniform temperature around the coil, enhancing temperature, and consequently smoke generation performance. In block 508, the value of Tau is calculated based on the indirectly measured temperature. The calculation of Tau was discussed above and may be referred to as a model of the thermal or temperature variance. The model may monitor the value of Tau based on the varying temperature in real-time in block 510. If the value of Tau increases above a predetermined amount as in block 512, an alarm is triggered. The predetermined amount may be two standard deviations above the average in one embodiment. The alarm may be a notification to the user to change the e-liquid container or the e-Cig may automatically shut-down to prevent burning. The alarm may further provide a set "time left" for operation of the e-Cig with the current e-Liquid (e.g. 2 minutes of smoking or 10 puffs).

The modeling, monitoring and control system described herein may be a feedback system in which the real-time measurements and calculations (e.g. modeling) is performed periodically and updated. It is those updated values that are used to determine and identify anomalies (e.g. Tau value above the average). Accordingly, the coil resistance may be monitored and the value of Tau constantly updated so that an anomaly may be identified quickly.

Figure 6:
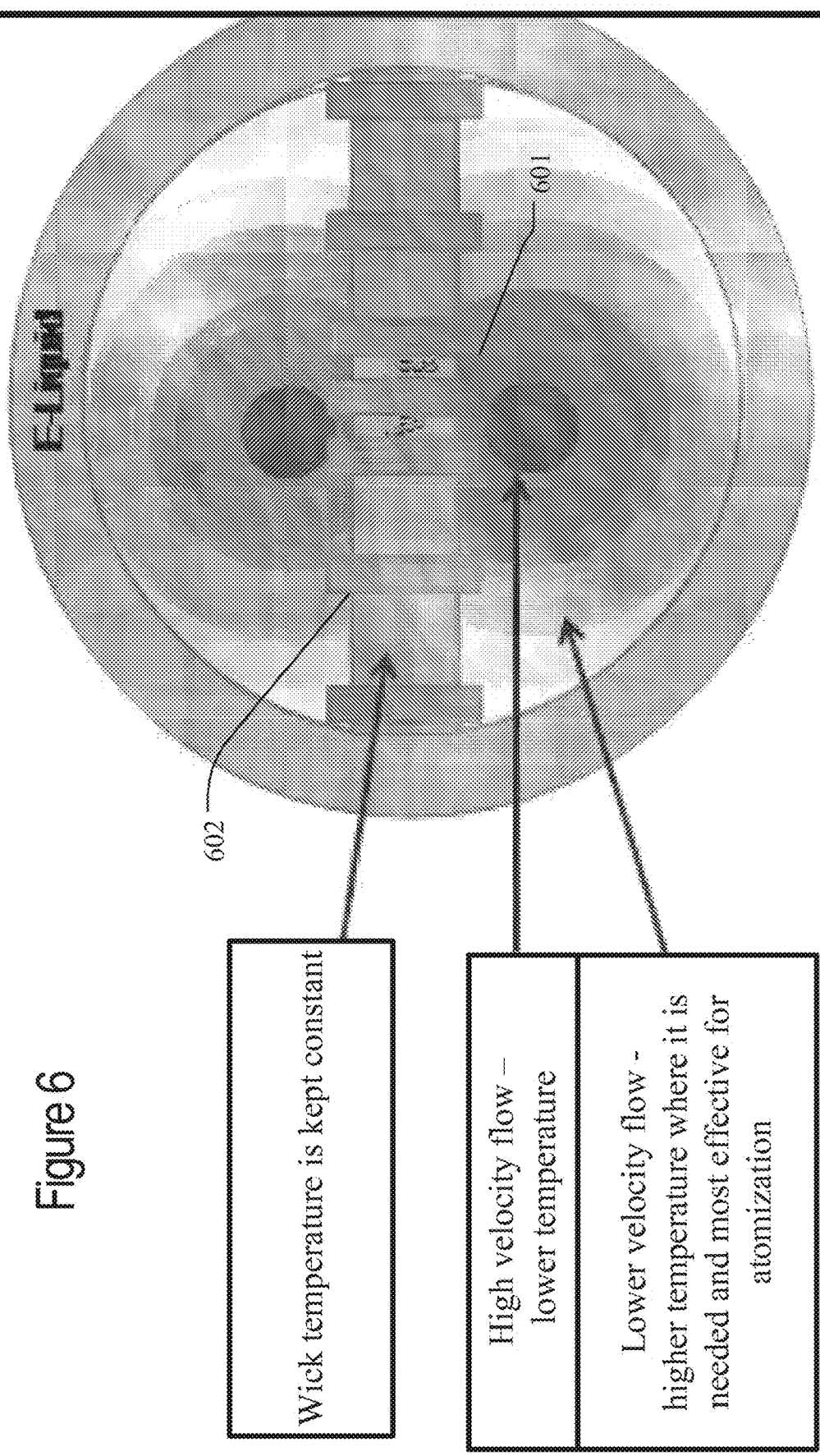
FIG. 6 illustrates a modified coil winding.

In other embodiments, the response to an increase in temperature (or an increase in Tau) may result in alternative changes to the e-Cig. In one embodiment, the coil arrangement may be modified to reduce the geometric unevenness of the flow. For example, as the flow in the middle of the cartomizer is faster than in the vicinity of the walls and more heat is removed from the middle; so the coil shape can be modified to deliver more power at the middle of the flow FIG. 6 illustrates a modified coil winding. In particular, the coil winding at a center portion 601 is denser than at a peripheral or side portion(s) 602. Accordingly, the temperature at the center portion 601 is higher than at the side portions 602. The difference in density of the coil may result in the wick temperature being kept constant because the high velocity flow at the center portion 601 compensates for the higher temperature that would otherwise result for the denser coil winding. Likewise, the lower velocity flow at the side portions 602 would result in a higher temperature, but the coil density is reduced to moderate the temperature.

In a typical winding, the coil wire diameter may be about 0.12, and the wire length prior to winding is about 33-34 mm. Following a winding operation, the coil may vary between 1 and 5 mm. with about 7 wraps, whose spacing varies so as to achieve a relatively loose winding near the ends of the coil, and a relatively tight winding centrally, as shown in FIG. 6. A typical coil length may be approximately 0.84 mm. It may be desirable to vary a uniform coil loop interspacing so as to provide relative reduction of 25-50% in the central portion 601 (e.g., the central ⅓ of the coil as compared with the peripheral regions 602 (regions that are outside the central region). The central section 601 may be defined in different ways, as a fraction of the total length of the coil. Values of ⅕ (a narrow central section) to ¾ (a broad central section) may be used. Various step-wise and continuous variations in gaps between coil loops are also possible.

In other embodiments, there may be a smart chip with a feedback loop to check the temperature of the coil at certain intervals during a puff. The heating coil serves as the temperature sensor in the system. Accordingly, it may be made of a conductor whose resistance changes with temperature. Such materials include iron, copper, tungsten, as well as other materials. Each material can be coated with nickel if necessary to minimize tarnish. During a puff, the controller chip can measure the voltage across a shunt resistor and determine the current passing through the coil. This indirectly indicates the resistance in the coil which indirectly indicates the temperature since that resistance varies as temperature changes. Alternatively, the controller may allow for a small voltage and measure the associated current directly through the coil. This would enable real time resistance and temperature determinations.

Since all current management is done electronically there may be certain time phases in which current is not applied through the coil. In those times, resistance of coil is measured and compared to a calibration curve. Since resistance is proportional to temperature this measurement may be calibrated to coil temperature. The whole measurement may require only a few microseconds to a few milliseconds. The actual power supplied to the coil during the measurement may small, not influencing battery lifetime significantly. Further, it may also create minimal power which prevents additional heating of the coil. The measurement may be applied when there is no current flow through the coil. The controller chip can then adjust its current output in response to deviations from a desired level in order to restore the temperature at the desired level.

The adjustments made in response to the real-time monitoring described herein that identify anomalies (e.g. burning or liquid depletion) may be used to solve various problems including:

1) Overheating;
2) Uniform smoke level;
3) Uniform vapor/mist/smoke temperature;
4) Improved battery efficiency and battery life—10%-20%;
5) Increases the useful operating life span of the wick, ensuring that first puffs will have more smoke (without the need for priming);
6) Better shelf life;
7) Ability to adjust heat as materials are adjusted (e.g. changing a conventional heating coil to a ceramic heating element);
8) Non uniformity of heating wires supplied by vendors.

Using a smart controller that measures resistance, the requirement for tight tolerance on a heating wire may be increased. The controller can be used to measure the resistance and deliver the correct heat to the heating wire.

As discussed with respect to FIG. 6, the coil wraps may be concentrated towards the center of the wick, i.e., the loop density of the coil is greater in the center than away from the center as one response to the monitoring. In other words, the interspaces between loops of the coil are smaller at and near the center than away from the center.

If the heating element is made of a ceramic filament that is coated with a heat-producing conductive spray, there may be certain advantages including:

1) Consistent resistance;
2) Large surface area to atomize, which minimized hotspots and burning;
3) Less heat stress on liquid; and
4) Longer shelf life of product.

As described, the resistance of the heating element (e.g. coil) may be used to determine temperature. The accuracy of the temperature determination may be based on the accuracy of the temperature measurement. However, production tolerances (e.g. of the heating element size, wires length, or others) may influence the temperature measurement and potentially impair accuracy. Accordingly, a calibration process may be used for improving the resistance value measurement. The calibration process may enable characterization of each cartomizer (e.g. when it is installed on the e-Cig) so that proper resistance values are used for more accurate temperature determination.

Figure 7:
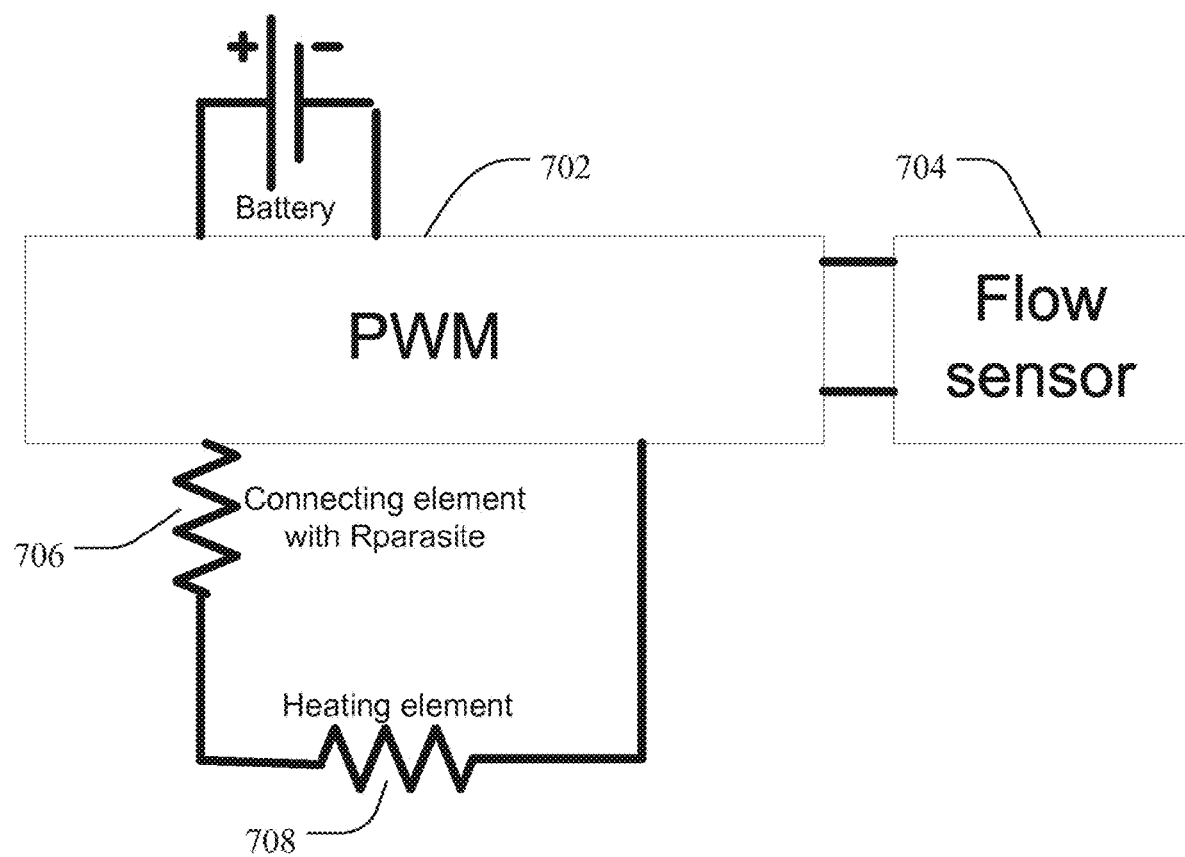
FIG. 7 is a diagram illustrating the resistors.

FIG. 7 is a diagram illustrating the resistors. A pulse-width modulator ("PWM") 702 is connected with the battery power for providing power, such as to the flow sensor 704. A connecting element 706 connects the PWM 702 with the heating element. The heating element includes a resistor 708 as does the connecting element.

The calibration process includes a total resistance calculation of the of coil and connection wires to the controller (for example a PWM power controller chip) of "Rtotal" is: Rtotal=Rparasite+Rcoil, where Rparasite is the resistance of the connecting element 706, which is the wire leading to the coil. Rcoil is the resistance of the resistor 708 for the heating element.

The connecting element 706 may include any connecting wires or elements that conduct electrical power from power supply PWM 702. Since the heating element (e.g. coil) performs the heating, its resistor 708 may have a resistance that will be much higher than the connecting wires of the connecting element 706. In other words, Rparasite may be much less than Rcoil.

Accordingly, the material selected may be also contributing to the accuracy of the resistance calculation. A material may be selected with relatively low dependence of resistance on temperature, such that the temperature coefficient per degree C. would prevent complex calculation and improve accuracy. However, a material with linear or more complex temperature behavior may be used when its properties are well known. Accordingly, it can be assumed that this coefficient will have negligible effect on combined resistance Rtotal.

The heating element may be a material with high positive temperature coefficients ("PCT"). These materials may enable a self-protection against high temperature due to increased resistance. The resistance may increase when temperature rises, which may create an intrinsic mechanism that reduces current if temperature rises. However, the proposed method may be utilized with a relatively low temperature coefficient, and with the ability to perform adequate calculations in the chip based on the algorithms described herein.

Determination or calculation of the temperature may consider the thermal behavior of the coil. The resulting equations may be:

$$R\text{coil} = R\text{coil}_{T=T0}(1+\alpha\Delta T) \quad \text{Equation 8}$$

$$R\text{total} = R\text{parasite} + R\text{coil}_{T=T0}(1+\alpha\Delta T) = R\text{parasite} + R\text{coil}_{T=T0}(1+\alpha(T-T0)) \quad \text{Equation 9}$$

T0 may be 20 or 25 Celsius in one example and $\alpha$ is the temperature coefficient of the coil, which is material constant the temperature. For the resistance to be measured with necessary accuracy, the resistance of the coil at T0 should be known (where T0 reference temp) and the connecting wires should have a known length, such that their resistance can be measured.

The temperature of the wick may then be measured if total resistance is measured:

$$T = \left(\frac{R\text{total}}{R\text{parasite} + R\text{coil}_{T=T0}} - 1\right)\frac{1}{\alpha} + T0 \quad \text{Equation 10}$$

Both the coil and connecting wires have production tolerances, but since the resistance of coil is much higher, the effect of tolerance in coil production has a higher effect. Accordingly, calibration of coil resistance may be used to reduce temperature measurement inaccuracies.

In the embodiment, where the battery assembly and cartomizer containing heating element (coil) assembly are not separable, the tolerances may be calibrated in the production line. For products where the battery is rechargeable and cartomizers are disposable, there may be a need to verify the cartomizer coil resistance via calibration.

Coil calibration may include:

a) Verifying an accurate assembly line and using high quality repeatable materials to enable quality assurance measurements.

b) Measuring every cartomizer and enabling the data to be transferred to a power processor using NFC or other low energy communication device to the processor that command the PWM.

c) Calibrating results at a point where the temperature is known. This may utilize the following equation 11 to calculate $Rcoil_{T=T0}$ since Rparasite and material properties are known and temperature T is measured.

$$T = \left(\frac{Rtotal}{Rparasite + Rcoil_{T=T0}} - 1\right)\frac{1}{\alpha} + T0 \qquad \text{Equation 11}$$

where T0 is the ambient temperature, at the time of connection the cartomizer to the battery. In one embodiment, ambient temperature may be measured by a smartphone and transferred by communication means to the PWM processor. In another embodiment, ambient temperature may be measured in the cigarette case with communication between the e-Cig and case. In another embodiment, ambient temperature may be measured using a temperature sensor connected or part of the processor, or attached to the battery. The parameter $Rcoil_{T=T0}$ is the reference resistance and may be kept by the cartomizer. Accordingly, for every replacement of cartomizer this parameter should be checked.

In the embodiment, where the cartomizer may be an independent assembly and there is no communication between the cartomizer and controller, there may be a periodic resistance measurement that could be continuously invoked. This may achieve nothing when the circuit is open, and be activated when the circuit is first closed with a freshly-installed cartomizer. These measurements may be done using the minimal power and for a short time to reduce heat creation. An exemplary interval is in the range of a few seconds to a few minutes. These measurements may also enable the ability to identify when cartomizer is replaced.

In an alternative embodiment from that shown in FIG. 7, the power to the heating coil may be via a PWM (smart controller). This device regulates the voltage to the heating coil and thereby regulates the power to the heating coil. In addition, because it controls the voltage output to the heating coil it may also determine the heating coil wire resistance. This may be done by limiting the voltage to the heating coil intermittently during the period of a puff. In this small period the controller will deliver a small voltage to the heating coil and measure the returning current in the smart controller. The resistance of the heating coil would thereby be determined in real time. In this way the smart controller would use this real time data to determine the temperature and liquid level in the cigarette.

Figure 8:
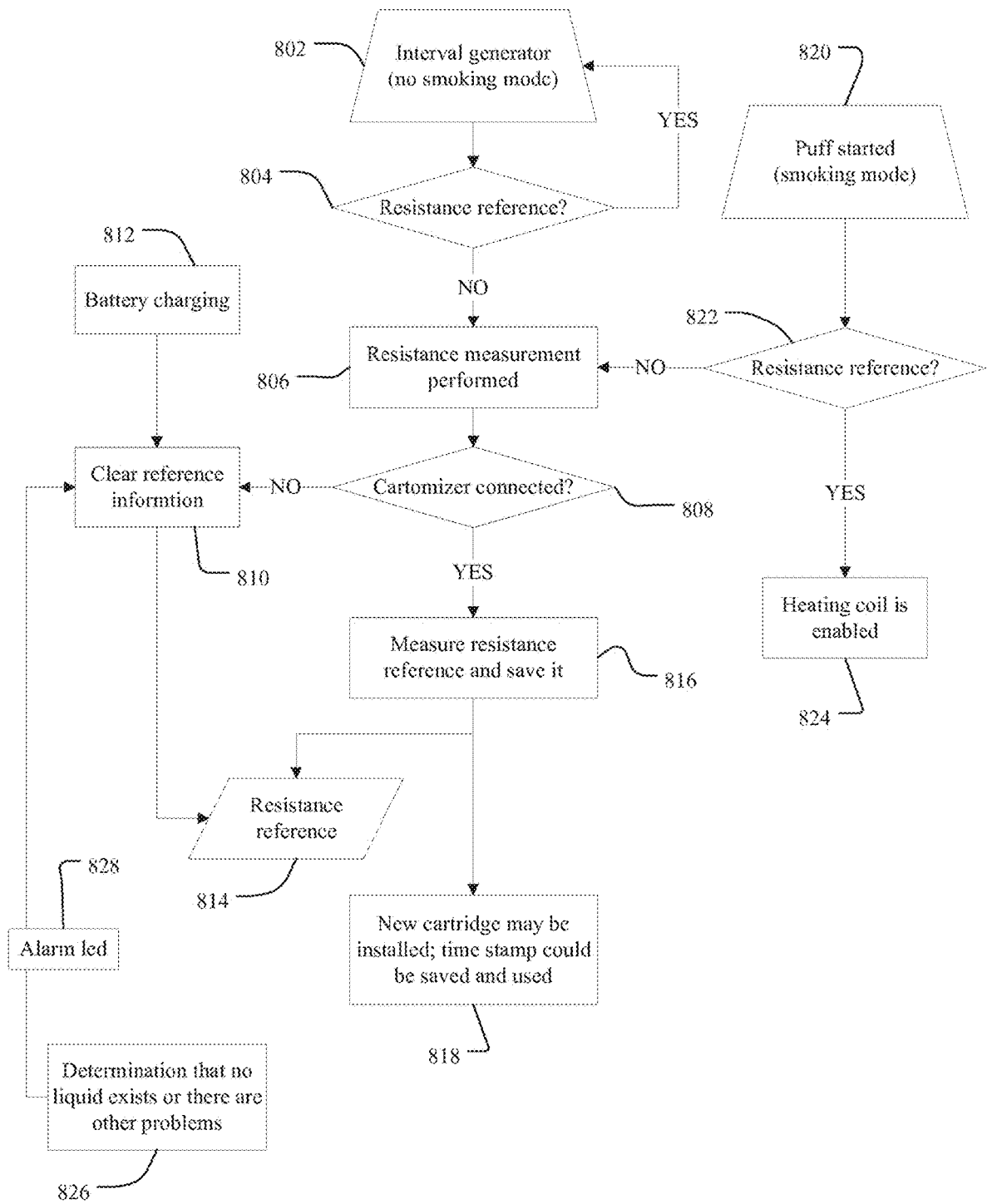
FIG. 8 is a chart illustrating exemplary resistance measurement.

FIG. 8 is a chart illustrating exemplary resistance measurement. In particular, FIG. 8 illustrates an exemplary algorithm for measuring resistance which is used to determine temperature.

Resistance measurements for calibration are scheduled at time intervals in block 802 or when a puff is started in block 820. Preliminary additional conditions for measurement may include: 1) when battery is not at charging phase; 2) the e-Cig is in a waiting state; and or 3) no information about resistance reference exists. In blocks 804 and 822, a determination is made as to whether a resistance reference value exists. If the resistance does exist in block 804, the interval generator 802 continues. If the resistance reference does exist in block 822, the heating element or coil is enabled in block 824. If the resistance reference does not exist in either blocks 804, 822, a resistance measurement is performed in block 806.

Based on the resistance measurement, a determination may be made as to whether the cartomizer is connected in block 808. If the resistance is too high it show that cartomizer may not be connected. In one embodiment, the total resistance may be in the order of magnitude of 0.2-10 ohm, and if resistance is higher than 100 ohm, the cartomizer is not connected. If the measurement is above the limit for example 10-100 ohm a problem may be identified. An abnormally high resistance value can reflect that no cartomizer is connected and the reference information can be cleared in block 810. This enables a reduction of tolerance of resistance of coil production and enables recognition of cartomizer type if different resistances will be used for each cartomizer. Different cartomizers may have different resistance reference points. This ability may be used when there is a need to replace a cartomizer where the calculation of heat parameters using Tau as described above may lead to a conclusion that the cartomizer is not properly functioning or has other problems.

In block 812, when the battery is charging, the reference information may also be cleared. When a cartomizer is connected in block 808, the resistance measurement is saved in block 816. The resistance reference value 814 is either saved in block 816 or cleared as in block 810. A new cartridge can be installed and a time stamp may be saved and used. In block 826, when there is a determination that the liquid is out or running out, or that there is another problem, an alarm LED may be triggered in block 828. The reference information may be cleared in block 810 after the determination of block 826.

The process may be used to establish or maintain a temperature after puff for a few minutes above a certain level (e.g. 40-50 C) to enable a "better start" for the next puff. Prolonged heat may maintain at a low temperature.

A "computer-readable medium," "machine readable medium," "propagated-signal" medium, and/or "signal-bearing medium" may comprise any device that includes, stores, communicates, propagates, or transports software for use by or in connection with an instruction executable system, apparatus, or device. The machine-readable medium may selectively be, but not limited to, an electronic, magnetic, optical, electromagnetic, infrared, or semiconductor system, apparatus, device, or propagation medium. A non-exhaustive list of examples of a machine-readable medium would include: an electrical connection "electronic" having one or more wires, a portable magnetic or optical disk, a volatile memory such as a Random Access Memory "RAM", a Read-Only Memory "ROM", an Erasable Programmable Read-Only Memory (EPROM or Flash memory), or an optical fiber. A machine-readable medium may also include a tangible medium upon which software is printed, as the software may be electronically stored as an image or in another format (e.g., through an optical scan), then compiled, and/or interpreted or otherwise processed. The processed medium may then be stored in a computer and or machine memory.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

The invention claimed is:

1. An electronic device comprising:
   a container to hold a vapor-forming material;
   a heating element configured to heat the vapor-forming material during a puff event time period, the puff event time period including a plurality of heating time intervals and at least one measurement interval;
   a power supply connected to the heating element; and
   a controller connected to the power supply, the controller configured to
      apply a heating current to the heating element to heat the vapor-forming material during the plurality of heating time intervals,
      cease application of the heating current to the heating element during the at least one measurement interval,
      measure a resistance of the heating element during the at least one measurement interval,
      determine a temperature of the heating element based on the resistance of the heating element,
      compute a heat transfer time constant of the heating element based on the temperature of the heating element, and
      determine whether the vapor-forming material is depleted based on the heat transfer time constant of the heating element.

2. The electronic device of claim 1, wherein the controller is configured to determine the temperature of the heating element based on the resistance of the heating element and a resistance reference value associated with the electronic device.

3. The electronic device of claim 1, wherein the heating element is a heating coil.

4. The electronic device of claim 3, wherein
   the vapor-forming material is a liquid formulation; and
   the electronic device includes a wick configured to draw the liquid formulation from the container, and the heating coil is wrapped around the wick, and configured to heat liquid formulation on the wick.

5. The electronic device of claim 4, wherein windings of the heating coil around the wick are spaced apart unevenly along a length of the wick.

6. The electronic device of claim 1, wherein the controller is configured to determine whether to output an alert based on the temperature of the heating element.

7. The electronic device of claim 1, wherein the controller is configured to determine whether to shut down the electronic device based on the temperature of the heating element.

8. A method of operating an electronic device including a power supply, a heating element, a controller and a container holding a vapor-forming material, the method comprising:
   applying, by the controller, a heating current to the heating element to heat the vapor-forming material during a plurality of heating time intervals of a puff event time period, the puff event time period including the plurality of heating time intervals and at least one measurement interval,
   ceasing, by the controller, application of the heating current to the heating element during the at least one measurement interval,
   measuring, by the controller, a resistance of the heating element during the at least one measurement interval;
   determining, by the controller, a temperature of the heating element based on the resistance of the heating element;
   computing a heat transfer time constant of the heating element based on the temperature of the heating element; and
   determining whether the vapor-forming material is depleted based on the heat transfer time constant of the heating element.

9. The method of claim 8, further comprising:
   determining whether to output an alert based on the temperature of the heating element.

10. The method of claim 8, wherein
    the vapor-forming material is a liquid,
    the container is a reservoir storing the liquid, and
    the method further includes
       determining whether the reservoir is depleted based on the heat transfer time constant of the heating element; and
       outputting an alert in response to determining that the reservoir is depleted.

11. The method of claim 8, further comprising:
    determining whether to shut down the electronic device based on the temperature of the heating element.

12. The method of claim 8, further comprising:
    determining whether the vapor-forming material is depleted based on the temperature of the heating element; and
    shutting down the electronic device in response to determining that the vapor-forming material is depleted.

* * * * *